United States Patent [19]

Thompson

[11] Patent Number: 4,513,146
[45] Date of Patent: Apr. 23, 1985

[54] METHOD FOR PRODUCING ESTERS FROM HIGHLY HINDERED CARBOXYLIC ACIDS OR THEIR SALTS, AND CARBONATES

[75] Inventor: Ralph B. Thompson, Oakbrook, Ill.

[73] Assignee: PPG Industries, Inc., Pittsburgh, Pa.

[21] Appl. No.: 422,221

[22] Filed: Sep. 23, 1982

[51] Int. Cl.³ .............................................. C07C 69/02
[52] U.S. Cl. ........................................ 560/231; 560/8;
560/9; 560/19; 560/55; 560/81; 560/105;
560/147; 560/155; 560/179; 560/190; 560/205
[58] Field of Search .................... 260/465 D; 560/103,
560/231, 234, 8, 9, 19, 55, 81, 105, 147, 155,
179, 190, 205

[56] References Cited

U.S. PATENT DOCUMENTS

| | | | |
|---|---|---|---|
| 1,781,050 | 11/1930 | Cade | 560/103 |
| 2,448,767 | 9/1948 | Carlson | 260/284 |
| 2,659,750 | 11/1953 | Bell et al. | 560/103 X |
| 3,013,054 | 12/1961 | Richter | 260/473 |
| 3,639,451 | 2/1972 | Ebert | 560/103 X |
| 3,976,635 | 8/1976 | Itoh | 560/103 X |
| 4,254,276 | 3/1981 | Iori et al. | 560/64 |
| 4,332,738 | 6/1982 | Benitel et al. | 260/410.6 |
| 4,362,670 | 12/1982 | Woo | 260/465 K |

Primary Examiner—Dolph H. Torrence

Attorney, Agent, or Firm—George D. Morris

[57] ABSTRACT

Ester is produced by reacting highly hindered carboxylic acid or salt thereof represented by the formula

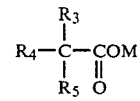

wherein
a. $R_3$, $R_4$, and $R_5$ are each independently a monovalent organo group, and
b. M is hydrogen, monovalent metal, or the monovalent fractional part of a polyvalent metal, with organic carbonate represented by the formula

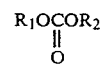

wherein $R_1$ and $R_2$ are each independently monovalent organic groups which may be the same or different, and wherein the alpha carbon of at least one of $R_1$ and $R_2$ is substantially sterically unhindered.

30 Claims, No Drawings

METHOD FOR PRODUCING ESTERS FROM HIGHLY HINDERED CARBOXYLIC ACIDS OR THEIR SALTS, AND CARBONATES

It is frequently desired to convert highly hindered carboxylic acid or a salt thereof, to ester. It has now been discovered that many organic carbonates are useful to effect this conversion. Accordingly, the present invention is a method comprising reacting highly hindered carboxylic acid or salt thereof represented by the formula

wherein $R_3$, $R_4$ and $R_5$ are each independently a monovalent organo group and M is hydrogen, monovalent metal or the monovalent fractional part of a polyvalent metal, with organic carbonate represented by the formula

wherein $R_1$ and $R_2$ are each independently monovalent organic groups which may be the same or different, and wherein the alpha carbon of at least one of $R_1$ and $R_2$ is substantially sterically unhindered, to produce carboxylic acid ester.

Substantially any monovalent organo groups which do not preclude ester formation may be used for $R_3$, $R_4$, and $R_5$, provided they are sterically compatible in the compound. They may be simple or they may be highly complex. Examples of organo groups which may be used include alkyl, alkenyl, aryl, (cycloalkyl)alkyl, aralkyl and cycloalkyl. Such groups may be substituted or unsubstituted. They may themselves be inert to the conditions of the reaction or they may contain groups such as mercapto, hydroxyl, amino, selenyl or carboxyl, which are reactive with organic carbonate. When an aryl group or a group containing an aryl portion is used, it may be homocyclic or heterocyclic; it may comprise a single ring or it may comprise a ring assembly. While polycarboxylic acids may be used, monocarboxylic acids are preferred. Only one carboxylic acid or salt thereof may be employed or a plurality of such materials may be used, as desired.

Often $R_3$, $R_4$ and $R_5$ are each independently an alkyl group. Any alkyl group may be straight or branched, but usually they are all straight. Typically each alkyl group has from 1 to about 20 carbon atoms. Often each alkyl group has from 1 to about 10 carbon atoms. Preferably $R_4$ is an alkyl group having from 1 to about 6 carbon atoms while $R_3$ and $R_5$ are each independently methyl or ethyl. It is especially preferred that $R_4$ have from 1 to about 6 carbon atoms while $R_3$ and $R_5$ are each methyl. The alkyl groups are usually unsubstituted, but any of them may contain one or more substituents of a minor nature that do not render the highly hindered carboxylic acid or salt thereof unsuited for its intended purpose. The substituents may be reactive or unreactive under the conditions of the reaction, but usually they are unreactive. Examples of suitable highly hindered carboxylic acids and salts of the class include 2,2-dimethylpropanoic acid, 2,2-dimethylbutanoic acid, 2,2-dimethyloctanoic acid, and the sodium and potassium salts thereof.

The identity of M may vary widely. Typically M is hydrogen, alkali metal or the monovalent fractional part of alkaline earth metal. Hydrogen, sodium or potassium are most frequently used.

The alpha carbon of at least one of $R_1$ and $R_2$ should be substantially unhindered so that one of these groups may replace the carboxyl hydrogen or the carboxyl metal to form the ester.

Typically $R_1$ is alkyl, alpha,beta-saturated alkenyl, aralkyl, (cycloalkyl)alkyl, cycloalkyl or lower aryl, and $R_2$ is alkyl, alpha,beta-saturated alkenyl, aralkyl or (cycloalkyl)alkyl. When alkyl is employed, it usually has from 1 to about 20 carbon atoms, often from 1 to about 10 carbon atoms. Lower alkyl having from 1 to about 4 carbon atoms is preferred. Methyl and ethyl are especially preferred. The alpha,beta-saturated alkenyl used generally has from 3 to about 10 carbon atoms; allyl is preferred. When aralkyl is employed, the aryl portion generally contains from 6 to about 10 carbon atoms and the alkyl portion usually contains from 1 to about 10 carbon atoms; benzyl is preferred. When (cycloalkyl)alkyl is used, the cycloalkyl portion generally contains from about 6 to about 8 carbon atoms and the alkyl portion typically contains from 1 to about 10 carbon atoms; cyclohexylmethyl is preferred. The cycloalkyl typically has from about 6 to about 8 carbon atoms; cyclohexyl is preferred. The lower aryl usually has from 6 to about 10 carbon atoms; phenyl is preferred. These groups are usually unsubstituted, although one or more minor substituents which do not render the organic carbonate unsuitable for its intended purpose may be present on any of the groups. Similarly, those groups having one or more rings are usually homocyclic, but one or more hetero atoms may be present so long as they do not seriously interfere with ester formation. The aliphatic groups and the aliphatic portions of hybrid groups such as aralkyl may be straight or branched, but it is preferred they be straight. Only one organic carbonate or a plurality of organic carbonates may be used as desired.

When a mixed organic carbonate, that is, an organic carbonate wherein $R_1$ and $R_2$ differ, is employed, it has been found that the reaction generally favors replacement of the carboxyl hydrogen or metal by the organo group having the less sterically hindered alpha carbon. It is ordinarily no impediment if the alpha carbon of one of $R_1$ and $R_2$ is substantially sterically hindered, but the degree of steric hinderance of the alpha carbon of at least one of $R_1$ and $R_2$ should not be so great as to preclude ester formation, that is to say, the alpha carbon of at least one of $R_1$ and $R_2$ should be substantially unhindered.

Examples of organic carbonates which may be employed include dimethyl carbonate, ethyl methyl carbonate, diethyl carbonate, propyl methyl carbonate, isopropyl methyl carbonate, isopropyl ethyl carbonate, butyl methyl carbonate, secondary-butyl methyl carbonate, isobutyl methyl carbonate, tertiary-butyl methyl carbonate, cyclohexyl methyl carbonate, benzyl methyl carbonate, phenyl methyl carbonate and diallyl carbonate. It is preferred that at least one of $R_1$ and $R_2$ be methyl or ethyl. The particularly preferred organic carbonates are dimethyl carbonate and diethyl carbonate.

In many cases the preparation of esters from highly hindered carboxylic acids and alcohols by direct esterification is at best difficult and either produces poor yields of esters or none at all. The method of the present invention is especially advantageous in preparing ester from highly hindered carboxylic acid or highly hindered carboxylic acid salt since the use of organic carbonate often results in a higher yield of ester than that obtained by direct esterification using alcohol.

The reaction of highly hindered carboxylic acid or salt thereof with organic carbonate is usually conducted in the liquid phase. It may be carried out batchwise, continuously, semibatchwise or semicontinuously. When the organic carbonate is a liquid under the conditions of the reaction, it often acts as a solvent for the carboxylic acid or salt thereof. Typically, but not necessarily, excess organic carbonate is employed and this usually serves to dissolve the highly hindered carboxylic acid or salt thereof throughout the reaction. In many cases, one or more by-products of the reaction, most notably alchols, also tend to dissolve the carboxylic acid or salt thereof. Although extrinsic solvent is not ordinarily employed, it may be used when desired or when necessary to dissolve one or more of the reactants. Examples of suitable extrinsic solvents include methanol, ethanol, acetonitrile, benzene, toluene, dioxane, dimethylformamide and chlorinated solvents such as chloroform, methylene chloride, ethylene chloride, carbon tetrachloride and chlorobenzene. Only one extrinsic solvent or a plurality of extrinsic solvents may be used as desired. For many reactions, extrinsic solvent need not be introduced, and the reaction may be neat.

When extrinsic solvent is used, the weight ratio of extrinsic solvent to the highly hindered carboxylic acid or salt thereof initially present is subject to wide variation. Generally, the amount of solvent should be sufficient to dissolve the reactants and, when desired, the catalyst, at the reaction temperature. The weight ratio of inert solvent, when used, to the highly hindered carboxylic acid or salt thereof initially present is usually in the range of from about 0.01:1 to about 20:1. From about 0.1:1 to about 5:1 is preferred.

The temperatures at which the reaction is conducted may vary considerably, but ordinarily they are in the range of from about 100° C. to about 250° C. Temperatures in the range of from about 120° C. to about 200° C. are preferred.

The pressures at which the reaction is conducted are similarly susceptible to wide variation. Atmospheric and superatmospheric pressures are generally employed, although lesser pressures may sometimes be used. Generally the pressure is in the range of from about zero to about 6000 kilopascals, gauge, but higher pressures may be used. Preferably the pressure is in the range of from about zero to about 5000 kilopascals, gauge.

The reaction is generally conducted in the presence of catalyst. Exemplary catalysts which may be used include nitrogen-containing heterocyclic catalysts such as pyridine, 4-(dimethylamino)pyridine, imidazole, 2,6-lutidine and 2,4,6-collidine. Only a single catalyst or a mixture of catalysts may be used where desired. The preferred catalyst is 4-(dimethylamino)pyridine. In some cases catalyst need not be used.

The equivalent ratio of the catalyst to the highly hindered carboxylic acid or salt thereof initially present may vary widely, but usually it is in the range of from about 0.005:1 to about 0.5:1. It is preferred that the equivalent ratio be in the range of from about 0.01:1 to about 0.15:1.

Following preparation, the ester may be recovered from the reaction mixture by any of the various techniques known to the art. Distillation at reduced pressure is one such technique that is frequently employed.

The present invention is especially useful for the preparation of alkyl esters of highly hindered carboxylic acids. In such cases at least one of $R_1$ and $R_2$ in Formula II, above, is alkyl. Dialkyl carbonates are preferred for these alkylations.

The invention is further described in conjunction with the following example which is to be considered illustrative rather than limiting.

EXAMPLE

A 1-liter reactor equipped with an agitator, an automatic temperature controller, a pressure gauge, and an electric heating mantle was charged with 102 grams of 2,2-dimethylpropanoic acid, 175 grams of dimethyl carbonate and 2 grams of 4-(dimethylamino)pyridine. The reactor was sealed and heated. The temperatures and pressures at various times after heating was begun are shown in the Table.

TABLE

| Time, Hours:Minutes | Temperature, °C. | Pressure, Kilopascals, Gauge | Remarks |
| --- | --- | --- | --- |
| 0:00 | Room | Slight Vacuum | Heat On |
| 0:17 | 125 | Slight Pressure | |
| 1:02 | 175 | 1655 | |
| 1:30 | 175 | 2689 | |
| 3:05 | 175 | 3723 | |
| 4:50 | 175 | 4619 | Heat Off |

After the reactor had cooled to ambient temperature, the pressure was 552 kilopascals, gauge. The gas within the reactor was found to contain carbon dioxide. The pressure was released. Gas-liquid chromatographic analysis showed the liquid to contain 46.9 area percent methyl 2,2-dimethylpropionate, 31.4 area percent dimethyl carbonate, 19.1 area percent methanol and less than 0.1 are percent 2,2-dimethylpropionic acid.

Although the present invention has been described with reference to specific details of certain embodiments thereof, it is not intended that such details should be regarded as limitations upon the scope of the invention except insofar as they are included in the accompanying claims.

I claim:

1. A method comprising reacting highly hindered carboxylic acid or salt thereof represented by the formula

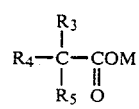

wherein
a. $R_3$, $R_4$, and $R_5$ are each independently a monovalent organo group, and
b. M is hydrogen, monovalent metal, or the monovalent fractional part of a polyvalent metal,
with organic carbonate represented by the formula

wherein $R_1$ and $R_2$ are each independently monovalent organic groups which may be the same or different, and wherein the alpha carbon of at least one of $R_1$ and $R_2$ is substantially sterically unhindered, to produce carboxylic acid ester.

2. The method of claim 1 wherein said reaction is conducted in the presence of catalyst.

3. The method of claim 2 wherein $R_1$ is alkyl, alpha,-beta-saturated alkenyl, aralkyl, (cycloalkyl)alkyl, cycloalkyl or lower aryl, and $R_2$ is alkyl, alpha,beta-saturated alkenyl, aralkyl or (cycloalkyl)alkyl.

4. The method of claim 2 wherein
   a. $R_1$ is alkyl having from 1 to about 20 carbon atoms, alpha,beta-saturated alkenyl having from 3 to about 10 carbon atoms, aralkyl wherein the aryl portion contains from 6 to about 10 carbon atoms and the alkyl portion contains from 1 to about 10 carbon atoms, (cycloalkyl)alkyl wherein the cycloalkyl portion contains from about 6 to about 8 carbon atoms and the alkyl portion contains from 1 to about 10 carbon atoms, cycloalkyl having from about 6 to about 8 carbon atoms, or lower aryl having from 6 to about 10 carbon atoms; and
   b. $R_2$ is alkyl having from 1 to about 20 carbon atoms, alpha,beta-saturated alkenyl having from 3 to about 10 carbon atoms, aralkyl wherein the aryl portion contains from 6 to about 10 carbon atoms and the alkyl portion contains from one to about 10 carbon atoms, or (cycloalkyl)alkyl wherein the cycloalkyl portion contains from about 6 to about 8 carbon atoms and the alkyl portion contains from 1 to about 10 carbon atoms.

5. The method of claim 2 wherein $R_1$ and $R_2$ are each independently alkyl having from 1 to about 10 carbon atoms.

6. The method of claim 2 wherein $R_2$ is methyl.

7. The method of claim 2 wherein $R_2$ is ethyl.

8. The method of claim 2 wherein said organic carbonate is dimethyl carbonate.

9. The method of claim 2 wherein said organic carbonate is diethyl carbonate.

10. The method of claim 2 wherein said highly hindered carboxylic acid is monocarboxylic acid.

11. The method of claim 2 wherein said catalyst is nitrogen-containing heterocyclic catalyst.

12. The method of claim 2 wherein said catalyst is 4-(dimethylamino)pyridine.

13. The method of claim 2 wherein said catalyst is pyridine.

14. The method of claim 2 wherein the equivalent ratio of said catalyst to said highly hindered carboxylic acid or salt thereof initially present is in the range of from about 0.005:1 to about 0.5:1.

15. The method of claim 2 wherein said reaction is conducted at a temperature in the range of from about 0° C. to about 250° C.

16. The method of claim 2 wherein said reaction is conducted at a pressure in the range of from about zero to about 6000 kilopascals, gauge.

17. The method of claim 2 wherein said reaction is conducted in the presence of extrinsic solvent.

18. The method of claim 17 wherein the weight ratio of said extrinsic solvent to said highly hindered carboxylic acid or salt thereof initially present is in the range of from about 0.01:1 to about 20:1.

19. The method of claim 2 wherein said reaction is neat.

20. The method of claim 2 wherein $R_3$, $R_4$ and $R_5$ are each independently an alkyl group.

21. The method of claim 20 wherein each alkyl group is straight.

22. The method of claim 20 wherein each alkyl group has from 1 to about 20 carbon atoms.

23. The method of claim 20 wherein $R_4$ contains from 1 to about 6 carbon atoms and $R_3$ and $R_5$ are each independently methyl or ethyl.

24. The method of claim 20 wherein $R_4$ contains from 1 to about 6 carbon atoms and $R_3$ and $R_4$ are each methyl.

25. The method of claim 2 wherein
   a. $R_1$ is alkyl having from 1 to about 20 carbon atoms, alpha,beta-saturated alkenyl having from 3 to about 10 carbon atoms, aralkyl wherein the aryl portion contains from 6 to about 10 carbon atoms and the alkyl portion contains from 1 to about 10 carbon atoms, (cycloalkyl)alkyl wherein the cycloalkyl portion contains from about 6 to about 8 carbon atoms and the alkyl portion contains from 1 to about 10 carbon atoms, cycloalkyl having from about 6 to about 8 carbon atoms, or lower aryl having from 6 to about 10 carbon atoms;
   b. $R_2$ is alkyl having from 1 to about 20 carbon atoms, alpha,beta-saturated alkenyl having from 3 to about 10 carbon atoms, aralkyl wherein the aryl portion contains from 6 to about 10 carbon atoms and the alkyl portion contains from one to about 10 carbon atoms, or (cycloalkyl)alkyl wherein the cycloalkyl portion contains from about 6 to about 8 carbon atoms and the alkyl portion contains from 1 to about 10 carbon atoms; and
   c. $R_3$, $R_4$ and $R_5$ are each independently an alkyl group having from 1 to about 20 carbon atoms.

26. The method of claim 25 wherein $R_1$ and $R_2$ are each independently alkyl having from 1 to about 10 carbon atoms.

27. The method of claim 26 wherein $R_4$ contains from 1 to about 6 carbon atoms and $R_3$ and $R_5$ are each independently methyl or ethyl.

28. The method of claim 27 wherein said organic carbonate is dimethyl carbonate or diethyl carbonate.

29. The method of claim 26 wherein $R_4$ contains from 1 to about 6 carbon atoms and $R_3$ and $R_5$ are each methyl.

30. The method of claim 29 wherein said organic carbonate is dimethyl carbonate or diethyl carbonate.

* * * * *